United States Patent [19]

Menchen et al.

[11] Patent Number: 5,188,934
[45] Date of Patent: Feb. 23, 1993

[54] 4,7-DICHLOROFLUORESCEIN DYES AS MOLECULAR PROBES

[75] Inventors: Steven M. Menchen, Fremont; Linda G. Lee, Palo Alto; Charles R. Connell, Redwood City; N. Davis Hershey, San Carlos; Vergine Chakerian, San Mateo; Sam Woo, Redwood City; Steven Fung, Palo Alto, all of Calif.

[73] Assignee: Applied Biosystems, Inc., Foster City, Calif.

[21] Appl. No.: 436,455

[22] Filed: Nov. 14, 1989

[51] Int. Cl.$^5$ .................. C12Q 1/68; C07D 311/78; C07D 311/94
[52] U.S. Cl. ............................ 435/6; 435/91; 435/172.3; 435/968; 436/800; 549/224; 549/382; 935/77
[58] Field of Search ............... 435/6, 91, 172.3, 968; 436/800; 549/224, 382; 935/78, 77

[56] References Cited

U.S. PATENT DOCUMENTS 4,855,225 8/1989 Fung ............................ 435/6

FOREIGN PATENT DOCUMENTS 8500360 9/1985 United Kingdom .

OTHER PUBLICATIONS

Marshall, P. N. "Rules for Visible Absorption Spectra of Halogenated Fluorescein Dyes", Histochem. J. 7(3)229-303 1975.
Pringle et al., DNA Core Facilities Newsletter, vol. 1, pp. 15-21 (1988).
Smith et al., Meth. Enzymol., vol. 155, pp. 260-301 (1987).
Connell et al., Biotechniques, vol. 5, pp. 342-348 (1987).
Karger et al., Nucleic Acids Research, vol. 19, pp. 4955-4962 (1991).
Wehry, chapter 3 in Guilbault, editor, Practical Fluorescence, 2nd Ed., (Marcel Dekker, New York, 1990).
Wehry, chapter 4 in Guilbault, editor, Practical Fluorescence, 2nd Ed., (Marcel Dekker, New York, 1990).
Haugland, chapter 2 in Steiner, editor, Excited States of Biopolymers (Plenum Press, New York, 1983).
Kirkbright, chapter 9, in Bishop, editor, Indicators (Pergamon Press, Oxford).
Lee et al., Cytometry, vol. 10, pp. 151-164 (1989).
Pringle et al., DNA Core Facilities Newsletter, vol. 1, pp. 15-21 (1988).
Smith et al., Meth. Enzymol., vol. 155, pp. 260-301 (1987).
Prober et al., Science, vol. 238, pp. 336-341 (1987).
Smith et al., Nature, vol. 321, pp. 674-679 (1986).
Kambara et al., Biotechnology, vol. 6, pp. 816-821 (1988).

Primary Examiner—Amelia Burgess Yarbrough
Attorney, Agent, or Firm—Stephen C. Macevicz; Joseph H. Smith

[57] ABSTRACT

Long wavelength, narrow emission bandwidth fluorecein dyes are provided for detecting spacially overlapping target substances. The dyes comprise 4,7-dichlorofluoresceins, and particularly 1',2',7',8'-dibenzo-4,7-dichlorofluoresceins. Methods of using the dyes in automated DNA sequencing are described.

18 Claims, No Drawings

4,7-DICHLOROFLUORESCEIN DYES AS MOLECULAR PROBES

FIELD OF THE INVENTION

The invention relates generally to fluorescent labelling techniques, and more particularly, to the use of 4,7-dichlorofluoresceins for detecting multiple target substances in the same sample.

BACKGROUND

Many diagnostic and analytical techniques require that multiple target substances in the same sample be labeled with distinguishable fluorescent tags, e.g. in flow cytometry as exemplified by Lanier et al, *J. Immunol.*, Vol. 132, Pgs. 151-156 (1984); and chromosome analysis as exemplified by Gray et al, *Chromosoma*, Vol 73, pgs. 9-27 (1979). This requirement is particularly difficult to satisfy in DNA sequence analysis where at least four spectrally resolvable dyes are needed in most automated procedures.

Presently there are two basic approaches to DNA sequence determination: the dideoxy chain termination method, e.g. Sanger et al, *Proc. Natl. Acad. Sci.*, Vol. 74, pgs. 5463-5467 (1977); and the chemical degradation method, e.g. Maxam et al, *Proc. Natl. Acad. Sci.*, Vol. 74, pgs.560-564 (1977). The chain termination method has been improved in several ways, and serves as the basis for all currently available automated DNA sequencing machines, e.g. Sanger et al, *J. Mol. Biol.*, Vol. 143, pgs. 161-178 (1980); Schreier et al, *J. Mol. Biol.*, Vol. 129, pgs. 169-172 (1979); Smith et al, *Nucleic Acids Research*, Vol. 13, pgs. 2399-2412 (1985); Smith et al, *Nature*, Vol. 321, pgs. 674-679 (1987); Prober et al, *Science*, Vol. 238, pgs. 336-341 (1987), Section II, *Meth. Enzymol.*, Vol. 155, pgs. 51-334 (1987); Church et al, *Science*, Vol 240, pgs. 185-188 (1988); and Connell et al, *Biotechniques*, Vol. 5, pgs. 342-348 (1987).

Both the chain termination and chemical degradation methods require the generation of one or more sets of labeled DNA fragments, each having a common origin and each terminating with a known base. The set or sets of fragments must then be separated by size to obtain sequence information. In both methods, the DNA fragments are separated by high resolution gel electrophoresis. In most automated DNA sequencing machines, fragments having different terminating bases are labeled with different fluorescent dyes, which are attached either to a primer, e.g. Smith et al (1987, cited above), or to the base of a terminal dideoxynucleotide, e.g. Prober et al (cited above). The labeled fragments are combined and loaded onto the same gel column for electrophoretic separation. Base sequence is determined by analyzing the fluorescent signals emitted by the fragments as they pass a stationary detector during the separation process.

Obtaining a set of dyes to label the different fragments is a major difficulty in such DNA sequencing systems. First, it is difficult to find three or more dyes that do not have significantly overlapping emission bands, since the typical emission band halfwidth for organic fluorescent dyes is about 40-80 nanometers (nm) and the width of the visible spectrum is only about 350-400 nm. Second, even when dyes with non-overlapping emission bands are found, the set may still be unsuitable for DNA sequencing if the respective fluorescent efficiencies are too low. For example, Pringle et al, DNA Core Facilities Newsletter, Vol. 1, pgs. 15-21 (1988), present data indicating that increased gel loading cannot compensate low fluorescent efficiencies. Third, when several fluorescent dyes are used concurrently, excitation becomes difficult because the absorption bands of the dyes are often widely separated. The most efficient excitation occurs when each dye is illuminated at the wavelength corresponding to its absorption band maximum. When several dyes are used one is often forced to make a trade off between the sensitivity of the detection system and the increased cost of providing separate excitation sources for each dye. Fourth, when the number of differently sized fragments in a single column of a gel is greater than a few hundred, the physiochemical properties of the dyes and the means by which they are linked to the fragments become critically important. The charge, molecular weight, and conformation of the dyes and linkers must not adversely affect the electrophoretic mobilities of closely sized fragments so that extensive band broadening occurs or so that band positions on the gel become reversed, thereby destroying the correspondence between the order of bands and the order of the bases in the nucleic acid whose sequence is to be determined. Finally, the fluorescent dyes must be compatible with the chemistry used to create or manipulate the fragments. For example, in the chain termination method, the dyes used to label primers and/or the dideoxy chain terminators must not interfere with the activity of the polymerase or reverse transcriptase employed.

Because of these severe constraints only a few sets of fluorescent dyes have been found that can be used in automated DNA sequencing and in other diagnostic and analytical techniques, e.g. Smith et al (1985, cited above); Prober et al (cited above); Hood et al, European patent application 8500960; and Connell et al (cited above).

In view of the above, many analytical and diagnostic techniques, such as DNA sequencing, would be significantly advanced by the availability of new sets of fluorescent dyes (1) which are physiochemically similar, (2) which permit detection of spacially overlapping target substances, such as closely spaced bands of DNA on a gel, (3) which extend the number of bases that can be determined on a single gel column by current methods of automated DNA sequencing, (4) which are amenable for use with a wide range of preparative and manipulative techniques, and (5) which otherwise satisfy the numerous requirements listed above.

SUMMARY OF THE INVENTION

The invention is directed to a method of concurrently detecting spacially overlapping target substances using 4,7-dichlorofluorescein dyes. The invention also includes methods of DNA sequence determination employing 4,7-dichlorofluorescein dyes, and compounds consisting of the 1',2',7',8'-dibènzo-5 (and 6-)carboxy-4,7,-dichlorofluoresceins defined by Formula I.

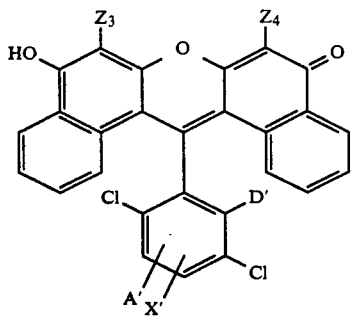

Formula I wherein:
- A' is hydrogen, fluoro, chloro, or a group, such as carboxyl, sulfonyl, or amino, that may be converted to a linking functionality; preferably A is a group that may be converted to a linking functionality;
- X' is a hydrogen, fluoro or chloro, such that whenever A' is a substituent of the 6 carbon atom X' is a substituent of the 5 carbon atom, and whenever A' is a substituent of the 5 carbon atom X' is a substituent of the 6 carbon atom; preferably, X' is hydrogen;
- $Z_3$ is hydrogen, fluoro, chloro, or a group, such as carboxyl, sulfonyl, or methylamino, that that may be converted to a linking functionality; preferably, $Z_3$ is hydrogen or chloro;
- $Z_4$ is hydrogen, fluoro, chloro, or a group, such as carboxyl, sulfonyl, or methylamino, that may be converted to a linking functionality; preferably, $Z_4$ is hydrogen or chloro; group;
- D' is fluoro, chloro, or an acidic anionic group; preferably, B' is carboxyl or sulfonyl, and most preferably B' is carboxyl; and
- wherein at least one of A', $Z_3$, and $Z_4$ is a group that may be converted to a linking functionality. Preferably, only one of A', $Z_3$, and $Z_4$ is a group that may be converted to a linking functionality.

Throughout, the *Colour Index* (Association of Textile Chemists, 2nd Ed., 1971) carbon numbering scheme is used, i.e. primed numbers refer to carbons in the xanthene structure and unprimed numbers refer to carbons in the 9'-phenyl.

The invention is based in part on the discovery that the fluorescent properties of 4,7-chloro-5- (and 6-)carboxyfluorescein and related dyes are highly favorable for use as molecular probes. Their emission band widths are generally 20–30 percent narrower than analogs lacking the 4,7-dichloro derivatives, their emission and absorption maxima are at wavelengths generally about 10–30 nm higher than analogs lacking the 4,7-dichloro derivatives, and their fluorescent efficiencies are high, in some cases being nearly triple those of analogs lacking the 4,7-dichloro derivatives.

DETAILED DESCRIPTION OF THE INVENTION

As mentioned above, the invention is based in part on the discovery of a class of fluorescein dyes that have absorption and emission maxima at unusually long wavelengths, narrow emission band widths and other favorable fluorescent properties. In addition, the invention includes the novel fluorescein analogs defined by Formula I as members of this class of dyes. These dyes permit the assembly of novel sets of spectrally resolvable, physiochemically similar dyes particularly useful in automated DNA sequence analysis.

As used herein the term "spectrally resolvable" in reference to a set of dyes means that the fluorescent emission bands of the dyes are sufficiently distinct, i.e. sufficiently non-overlapping, that target substances to which the respective dyes are attached, e.g. polynucleotides, can be distinguished on the basis of the fluorescent signal generated by the respective dyes by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21–76, in *Flow Cytometry: Instrumentation and Data Analysis* (Academic Press, New York, 1985).

The term "lower alkyl" as used herein directly or in connection with ethers denotes straight-chain and/or branched chain alkyl groups containing from 1–6 carbon atoms, e.g. the term includes methyl, ethyl, propyl, isopropyl, tert-butyl, isobutyl, and the like.

The term "halo" as used herein denotes the halogen atoms fluorine, chlorine, bromine, and iodine; more preferably, the term denotes fluorine or chlorine; and most preferably, the term denotes chlorine.

Preferably, the 4,7-chloro-5- (and 6-) carboxyfluorescein dyes of the invention include those defined by Formula II.

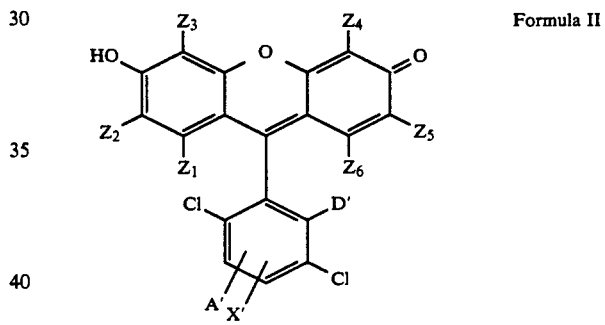

Formula II wherein:
- A', D' and X' are defined as above;
- $Z_1$ is hydrogen or, when taken with $Z_2$, benzo;
- $Z_2$, when taken alone, is hydrogen, halo, lower alkyl, lower alkyloxy, or a group, such as carboxyl, sulfonyl, or methylamino, that may be converted to an active linking functionality, or when taken with $Z_1$, $Z_2$ is benzo; preferably, when taken alone, $Z_2$ is hydrogen, methyl, ethyl, fluoro, chloro, methoxy, or ethoxy;
- $Z_3$ and $Z_4$ are hydrogen, halo, lower alkyl, lower alkyloxy, or a group, such as carboxyl, sulfonyl, or methylamino, that may be converted to a linking functionality; more preferably, $Z_3$ and $Z_4$ are hydrogen, fluoro, chloro, methyl, ethyl, methoxy, or ethoxy;
- $Z_5$ is hydrogen or, when taken with $Z_6$, benzo; and
- $Z_6$, when taken alone, is hydrogen, halo, lower alkyl, lower alkyloxy, or a group, such as carboxyl, sulfonyl, or methylamino, that may be converted to an active linking functionality, or when taken with $Z_5$, $Z_6$ is benzo; preferably, when taken alone, $Z_6$ is hydrogen, methyl, ethyl, fluoro, chloro, methoxy, or ethoxy;
- and wherein at least one of A, $Z_2$, $Z_3$, $Z_4$, and $Z_5$ is a group that may be converted to an linking functionality. Preferably, only one of A, $Z_2$, $Z_3$, $Z_4$, and $Z_5$ is a group that may be converted to an active linking functionality.

Many dyes of the invention are commercially available or can be synthesized by techniques known in the art, e.g. Ghatak et al, *J. Ind. Chem. Soc.*, Vol. 6, pgs. 465–471 (1929); and Khanna et al, U.S. Pat. No. 4,439,356. Alternatively, fluorescein analogs, i.e. A=B-=carboxyl, can be synthesized by reacting substituted resorcinol with substituted benzophenone or with substituted trimellitic acid in the presence of propionic acid, as illustrated in the examples. Sulfonylfluoresceins, i.e. A or B is sulfonyl, are synthesized following the methods disclosed by Lee et al, *Cytometry*, Vol. 10, pgs. 151–164 (1989), modified by substituting appropriate reactants to give 5- or 6-carboxyl- or or sulfonyl-fluorescein products. Preferably, when labeling polynucleotides in DNA sequencing the 5- and 6- isomers of the dyes are used separately because they typically have slightly different electrophoretic mobilities that can lead to band broadening if mixtures of the isomers are used. The 5- and 6- isomers of the dyes are readily separated by reverse phase HPLC, e.g. Edmundson et al, *Mol. Immunol.*, Vol. 21, pg. 561 (1984). Generally, it is believed that the first eluting peak is the 6- isomer and the second eluting peak is the 5- isomer.

Dyes of the invention can be attached to target substances by a variety of means well known in the art. For example, Haugland, *Handbook of Fluorescent Probes and Research Chemicals* (Molecular Probes, Inc., Eugene, 1989) provides guidance and examples of means for linking dyes to target substances. Substituent A is converted to a linking functionality that can be reacted with a complementary functionality on a target substance to form a linking group. The following table lists illustrative linking functionalities that can be formed whenever A is carboxyl sulfonyl or amine, suitable complementary functionalities, and the resulting linking groups suitable for use with the invention.

| Linking Functionality | Complementary Functionality | Linking Group |
|---|---|---|
| —NCS | —NH$_2$ | —NHCSNH— |
| 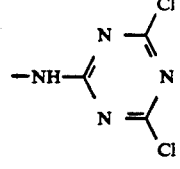 | —NH$_2$ | 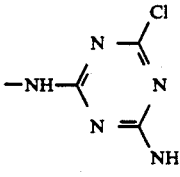 |
| —SO$_2$X | —NH$_2$ | —SO$_2$NH— |
| 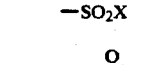 | —NH$_2$ | 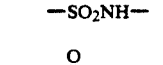 |
| —NH—C(O)—CH$_2$I | —SH | —NH—C(O)—CH$_2$S— |
| 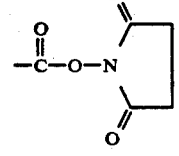 | —SH | 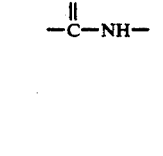 |

Preferably the linking functionality is isothiocyanate, sulfonyl chloride, 4,6-dichlorotriazinylamine, or succinimidyl carboxylate whenever the complementary functionality is amine. And preferably the linking functionality is maleimide, or iodoacetamide whenever the complementary functionality is sulfhydryl. Succinimidyl carboxylates can be formed by condensing the 5- and/or 6-carboxyls of the above dyes with N-hydroxysuccinimide using dicyclohexylcarbodiimide (DCC), e.g. as illustrated in examples 6 and 8 of Khanna et al, U.S. Pat. No. 4,318,846, and Kasai et al, *Anal. Chem.*, Vol. 47, pgs. 34–37 (1975). Accordingly, these references are incorporated by reference.

When dyes of the invention are used to label dideoxynucleotides for DNA sequencing, preferably they are linked to the 5 carbon of pyrimidine bases and to the 7 carbon of 7-deazapurine bases. For example, several suitable base labeling procedures have been reported that can be used with the invention, e.g. Gibson et al, *Nucleic Acids Research*, Vol. 15, pgs. 6455–6467 (1987); Gebeyehu et al, *Nucleic Acids Research*, Vol. 15, pgs. 4513–4535 (1987); Haralambidis et al, *Nucleic Acids Research*, Vol. 15, pgs. 4856–4876 (1987); and the like. Preferably, the linking group between the dye and a base is formed by reacting an N-hydroxysuccinimide (NHS) ester of a dye of the invention with an alkynylamino-derivatized base of a dideoxynucleotide. Preferably, the linking group is 3-carboxyamino-1-propynyl. The synthesis of such alkynylamino-derivatized dideoxynucleotides is taught by Hobbs et al in European patent application number 87305844.0, which is incorporated herein by reference. Briefly, the alkynylamino-derivatized dideoxynucleotides are formed by placing the appropriate halodideoxynucleoside (usually 5-iodopyrimidine and 7-iodo-7-deazapurine dideoxynucleosides as taught by Hobbs et al (cited above)) and Cu(I) in a flask, flushing with Ar to remove air, adding dry DMF, followed by addition of an alkynylamine, triethyl-amine and Pd(0). The reaction mixture can be stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

Target substances of the invention can be virtually anything that the dyes of the invention can be attached to. Preferably the dyes are covalently attached to the target substances. Target substances include proteins, polypeptides, peptides, polysaccharides, polynucleotides, lipids, and combinations and assemblages thereof, such as chromosomes, nuclei, living cells, such as bacteria, other microorganisms, and mammalian cells, tissues, and the like. As used herein the term "polynucleotide" means a single stranded or double stranded chain of DNA or RNA in the size range of about 10–1000 bases in length (if single stranded), or in the size range of about 10–1000 basepairs in length (if double stranded).

A number of complementary functionalities can be attached to the 5' or 3' ends of synthetic oligonucleotides and polynucleotides, e.g. amino groups, Fung et al, U.S. Pat. No. 4,757,141 and Miyoshi et al, U.S. Pat. No. 4,605,735; or sulfhydryl groups, Connolly, *Nucleic Acids Research*, Vol. 13, pgs. 4485–4502 (1985), and Spoat et al, *Nucleic Acids Research*, Vol. 15, pgs. 4837–4848 (1987).

Dyes of the invention are particularly well suited for identifying classes of polynucleotides that have been subjected to a biochemical separation procedure, such as gel electrophoresis, where a series of bands or spots of target substances having similar physiochemical properties, e.g. size, conformation, charge, hydrophobicity, or the like, are present in a linear or planar arrangement. As used herein, the term "bands" includes any spacial grouping or aggregation of target substance on the basis of similar or identical physiochemical properties. Usually bands arise in the separation of dye-polynucleotide conjugates by gel electrophoresis.

Classes of polynucleotides can arise in a variety of contexts. For example, they can arise as products of restriction enzyme digests. Preferably, classes identified in accordance with the invention are defined in terms of terminal nucleotides so that a correspondence is established between the four possible terminal bases and the members of a set of spectrally resolvable dyes. Such sets are readily assembled from the dyes of the invention by measuring emission and absorption bandwidths with commercially available spectrophotometers. More preferably, the classes arise in the context of the chemical or chain termination methods of DNA sequencing, and most preferably the classes arise in the context of the chain termination method. In either method dye-polynucleotide conjugates are separated by standard gel electrophoretic procedures, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid Research*, Vol. 1 (Springer-Verlag, Berlin, 1984). Preferably the type of gel is polyacrylamide having a concentration (weight to volume) of between about 2–20 percent. More preferably, the polyacrylamide gel concentration is between about 4–8 percent. Preferably the gel includes a strand separating, or denaturing, agent. Detailed procedures for constructing such gels are given by Maniatis et al., "Fractionation of Low Molecular Weight DNA and RNA in Polyacrylamide Gels Containing 98% Formamide or 7 M Urea," in *Methods in Enzymology*, Vol. 65, pgs. 299–305 (1980); Maniatis et al., "Chain Length Determination of Small Double- and Single-Stranded DNA Molecules by Polyacrylamide Gel Electrophoresis," *Biochemistry*, Vol. 14, pgs. 3787–3794, (1975); and Maniatis et al., *Molecular Cloning: A Laboratory Manual* (Cold Spring Harbor Laboratory, New York, 1982), pgs. 179–185. Accordingly these references are incorporated by reference. The optimal gel concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. By way of example, oligonucleotides having sizes in the range of between about 20–300 bases have been separated and detected in accordance with the invention in the following gel: 6 percent polyacrylamide made from 19 parts to 1 part acrylamide to bis-acrylamide, formed in a Tris-borate EDTA buffer at pH 8.3 (measured at 25° C.) with 48 percent (weight/volume) urea. The gel was run at 50° C.

The dye-polynucleotide conjugates on the gel are illuminated by standard means, e.g. high intensity mercury vapor lamps, lasers, or the like. Preferably, the dye-polynucleotides on the gel are illuminated by laser light generated by a argon ion laser, particularly the 488 and 514 nm emission lines of an argon ion laser. Several argon ion lasers are available commercially which lase simultaneously at these lines, e.g. Cyonics, Ltd. (Sunnyvale, Calif.) Model 2001, or the like.

In the chain termination method, dyes of the invention can be attached to either primers or dideoxynucleotides. Dyes can be linked to a complementary functionality on the 5' end of the primer, e.g following the teaching in Fung et al, U.S. Pat. No. 4,757,141 which is incorporated herein by reference; on the base of a primer; or on the base of a dideoxynucleotide, e.g. via the alkynylamino linking groups disclosed by Hobbs et al, European patent application number 87305844.0 which is incorporated herein by reference.

EXAMPLES

Example I. 4,7-dichloro-5-(and 6-)carboxyfluorescein ("ALF")

0.58 g of 3,6-dichlorotrimellitic acid, 0.72 g of resorcinol, 0.5 ml concentrated sulfuric acid, and 3 ml of propionic acid were refluxed 12 hours under argon. The reaction mixture was poured into 150 ml water; the precipitate was dried, taken into 3 ml pyridine and acetylated with 2 ml acetic anhydride for 1 hour. The acetylation mixture was taken into 100 ml ethyl acetate, washed with 1N hydrochloric acid, water, and evaporated to dryness. The residue was placed on 15 grams of silica gel and eluted with 50 ml ethyl acetate, then 4:1 ethyl acetate:methanol. Fractions containing UV active material with $R_f$ of about 0.2 (4:1 ethyl acetate:methanol/silica gel) were evaporated to dryness. This residue was dissolved in 10 ml methanol and then 1 ml of 4N sodium hydroxide was added. After 10 minutes, the reaction mixture was diluted to 200 ml with water and then 0.5 ml of concentrated hydrochloric acid was added. The total mixture was extracted with 200 ml of ethyl acetate, after which the ethyl acetate was dried with sodium sulfate and evaporated to dryness yielding 102 mg of yellow-green solid.

Example II. 4,7-dichloro-5-(and 6-) carboxyfluorescein N-hydroxysuccinimide (NHS) ester 13.7 mg of fluorescein from Example I, 3,3 mg of NHS, 6,4 mg DCC, and 1 ml ethyl acetate were stirred 0.5 hours. The solid was filtered, and the supernatant was washed three times with 1:1 brine:water, dried with sodium sulfate, and evaporated to dryness yielding 15 mg of NHS ester.

Example III. Conjugation of 4,7-dichloro-5-(and 6-) carboxyfluorescein with aminoalkyloligonucleotides 5 mg of NHS ester from Example II were dissolved in 20 ul of DMSO; 3 ul of this solution were added to a solution consisting of 20 ul of 1.0 mM 5'-aminohexylphosphate oligonucleotide (an 18-mer) in water and 10 ul of 1M sodium bicarbonate/sodium carbonate buffer, pH 9.0. After one hour in the dark, the solution was passed through a 10 ml Sephadex G-25 (medium) column with 0.1M triethylammonium acetate buffer, pH 7.0. The band of colored material eluting in the exclusion volume was collected. Reverse phase HPLC showed two major fluorescent peaks, corresponding to the 5- and 6- isomers of the dye conjugated onto the DNA. The peaks were collected, and the fluorescence spectra in 50% urea at pH 8.0 showed full width at half max of 34 nm with the emission maxima at 528 nm.

Example IV. 2',7'-dimethoxy-5-(and 6-)carboxy 4,7-dichlorofluorescein ("BUB")

The procedure of Example I was followed except that the following materials and quantities were substituted: 1,47 g 4-methoxyresorcinol, 0.60 g of 3,6-dichlorotrimellitic acid, 0.2 ml concentrated sulfuric acid, and 4 ml propionic acid. The procedure yielded 0.180 g of 4,7-dichloro-2',7'-dimethoxy-5-(and 6-)carboxyfluorescein.

Example V. 2',7'-dimethoxy-5-(and 6-)carboxy 4,7-dichlorofluorescein NHS ester 18 mg of this dye NHS ester were prepared as in Example II using 18 mg of dye from Example IV, 3.5 mg NHS, 6.4 mg DCC, and 2 ml ethyl acetate.

Example VI. Conjugation of 4,7-dichloro-2',7'-dimethoxy -5-(and 6-)carboxyfluorescein with aminoalkyloligonucleotide The procedure of Example III was followed using the dye NHS ester of Example V. The fluorescence spectra of the two peaks collected during reverse phase HPLC showed full widths at half max of 37 nm with emission maxima at 544 nm in 50% urea at pH 8.2.

Example VII. 2',7'-dimethoxy-4',5'-dichloro-5-(and 6-)carboxy-4,7-dichlorofluorescein ("LOU")

This dye was prepared from the dye of Example IV and sodium hypochlorite in aqueous sodium hydroxide.

Example VIII. 4,7-dichloro-2',7'-dimethoxy-4',5'-dichloro-5-(and 6-)carboxyfluorescein NHS ester 1.1 mg of this dye NHS ester was prepared from 0.7 mg of the dye from Example VII, 0.45 mg of NHS, 0.7 mg DCC, and 0.2 ml ethyl acetate as in Example II.

Example IX. Conjugation of 4,7-dichloro-2',7'-dimethoxy -4',5'-dichloro-5-(and 6-)carboxyfluorescein with aminoalkyloligonucleotides The dye oligonucleotide conjugate of this example was prepared as in Example III using the dye NHS ester from Example VIII. The fluorescence spectra of the two peaks collected during reverse phase HPLC showed full widths at half max of 38 nm with emission maxima at 558 nm in 50% urea at pH 8.2.

Example X. 1',2',7',8'-dibenzo-5-(and 6-)carboxy-4,7-dichlorofluorescein ("NAN")

First, 3,6-dichlorotrimellitic acid trichloride was prepared: A mixture of 0.5 g of 3,6-dichlorotrimellitic acid and 1.3 g of phosphorous pentachloride was heated at 130° C. for 40 minutes. The mixture was cooled to room temperature and poured into ice. The mixture was then extracted with 40 ml ether, the organic fraction was washed twice with 15 ml water, dried with MgSO$_4$, and concentrated to a clear oil (0.7 g). The acid trichloride was used without further purification. NAN was prepared as follows: A mixture of 2.7 g of 1,3-dihydroxynaphthalene, 2.84 g of 3,6-dichlorotrimellitic acid trichloride, and 8 ml of propionic acid was refluxed for 2 hours. Water (50 ml) and ethyl acetate (50 ml) were added. The layers were separated and the organic layer was extracted three times with 50 ml of 1M NaHCO$_3$. The aqueous solution was heated to boiling and acidified with concentrated HCl. The resulting red solid (0.2 g) was filtered and dried.

Example XI. 1',2',7',8'-dibenzo-4',5'-dichloro-5-(and 6-)carboxy-4,7-dichlorofluorescein ("DEB")

20 mg of NAN, sodium hydroxide (34 ul of a 15% solution), water (1 ml), and sodium hypochlorite (170 ul of a 5% solution) were combined. Reverse phase HPLC showed 92% reaction. The solution was acidified with HCl, extracted with 20 ml of ethyl acetate, dried (Na$_2$SO$_4$), and concentrated to 20 mg. The solid was purified by chromatography on a silica gel column (1" diameter×2" height), eluting with 600:60:16 methylene chloride:methanol:acetic acid. The dye solution was concentrated, and dilute HCl and ethyl acetate added. The organic phase was dried (MgSO$_4$) and concentrated to 20 mg of DEB.

Example XII. Formation of 1',2',7',8'-dibenzo-5-(and 6-)carboxy-4,7-dichlorofluorescein NHS ester NAN (10 mg) was dissolved in 2 ml of ethyl acetate, and NHS (10 mg) and DCC (5 mg) was added. After 20 minutes, the solution was dark red in color and a crystalline solid appeared. Thin layer chromatography on a silica gel using 600:60:16 methylene chloride:methanol:acetic acid showed complete conversion to the NHS ester. The ethyl acetate solution was washed with dilute HCl, dried (NaSO$_4$) and concentrated to a red solid (15 mg).

Example XIII. Using ALF-, BUB-, LOU-, and NAN-oligonucleotide conjugates as dye-labeled primers in DNA sequence analysis An all-fluorescein set of dyes was used to label DNA fragments in the chain termination approach employing the Applied Biosystems (Foster City, Calif.) Model 370A automated DNA sequencer. The manufacturer's protocol (User Bulletin DNA Sequencer Model 370, Issue No. 2, Aug. 12, 1987), which is incorporated by reference) was followed for amplification of the unknown DNA in M13 and preparation of separately labeled DNA fragments for gel electrophoretic separation. Dye-labeled primers were prepared as described in the examples above. That is, NHS esters of the respective dyes were prepared and reacted with the 5'-aminohexyl-derivatized M13 universal primer (5'-TCCCAGTCACGACGTTGT-3') to form the dye-labeled primers for the four separate dideoxy reaction mixtures. The following modifications were made to the standard protocol: 5-carboxy-4,7-dichlorofluorescein labeled the primer in the dideoxycytidine reaction, 2',7'-dimethoxy-5-carboxy-4,7-dichlorofluorescein labeled the primer in the dideoxyadenosine reaction, 2',7'-dimethoxy-4',5'-dichloro-6-carboxy-4,7-dichlorofluorescein labeled the primer in the dideoxyguanosine reaction, 1',2',7',8'-dibenzo-5-carboxy-4,7-dichlorofluorescein labeled the primer in the dideoxythymidine reaction, labeled DNA fragments from the respective reactions were combined in the following molar ratios for loading onto the gel: 1:1:4:2 ddC reaction:ddA reaction:ddG reaction:ddT reaction, and detection was accomplished with a modified filter wheel using 10-nm bandpass filters centered at 535, 550, 565, and 580 nm.

Example XIV. Using ALF-, BUB-, DEB-, and NAN-oligonucleotide conjugates as dye-labeled primers in DNA sequence analysis The same procedure was followed as described for Example XIII, except for the following: (i) 1',2',7',8'-dibenzo-4',5'-dichloro-5-carboxy-4,7-dichlorofluorescein labeled the primer in the dideoxyguanosine reaction, (ii) labeled DNA fragments from the respective reactions were combined in the following molar ratios for loading on the gel: 1:1:2:15 ddC reaction:ddA reaction:ddG reaction:ddT reaction, and (iii) 5 nm bandpass filters were centered at 540, 560, 580, and 610 nm.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

We claim:

1. A compound having the formula:

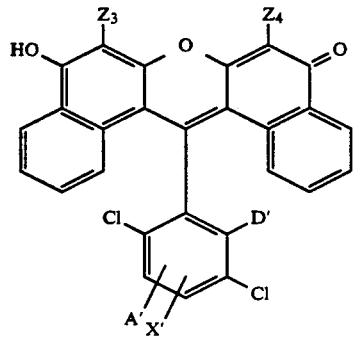

wherein:
A' is hydrogen, fluoro, chloro, or a group that may be converted to a linking functionality;
D' is fluoro, chloro, or an acidic anionic group;
X' is hydrogen, fluoro, or chloro;
$Z_3$ and $Z_4$ are separately hydrogen, halo, lower alkyl, lower alkyloxy, or a group that may be converted to a linking functionality; and
wherein at least one of A', $Z_3$, and $Z_4$ is a group that may be converted to a linking functionality.

2. The compound of claim 1 wherein A' is carboxyl, sulfonyl, or amino; B' is carboxyl or sulfonyl; X' is hydrogen; $Z_3$ and $Z_4$ are separately hydrogen, halo, methyl, methoxy, ethyl, ethoxy, carboxyl, sulfonyl, or methylamino.

3. The compound of claim 2 wherein only one of A', $Z_3$ and $Z_4$ is carboxyl, sulfonyl, methylamino, or amino.

4. The compound of claim 3 wherein A' and D' are carboxyl, $Z_3$ is hydrogen or chloro, and $Z_4$ is hydrogen or chloro.

5. A method of distinguishing polynucleotides having different terminal dideoxynucleotides in the chain termination method of DNA sequencing, the method comprising the steps of:
forming a mixture of a first, a second, a third, and a fourth class of polynucleotides,
each polynucleotide in the first class having a 3'-terminal dideoxyadenosine and being labeled with a first dye selected from the group consisting of 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, and 1',2',7',8'-dibenzo-4',5'-dichloro-5- and 6-carboxy-4,7-dichlorofluorescein,
each polynucleotide in the second class having a 3'-terminal dideoxythymidine and being labeled with a second dye selected from the group consisting of 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, and 1',2',7',8'-dibenzo-4',5'-dichloro-5- and 6-carboxy-4,7-dichlorofluorescein,
each polynucleotide in the third class having a 3'-terminal dideoxyguanosine and being labeled with a third dye selected from the group consisting of 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, and 1',2',7',8'-dibenzo-4',5'-dichloro-5- and 6-carboxy-4,7-dichlorofluorescein,
each polynucleotide in the fourth class having a b 3'-terminal dideoxycytosine and being labeled with a fourth dye selected from the group consisting of 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy- 4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, and 1',2',7',8'-dibenzo-4',5'-dichloro-5- and 6-carboxy-4,7-dichlorofluorescein, wherein the first, second, third, and fourth dyes are spectrally resolvable from one another;

electrophoretically separating on a gel the polynucleotides in the mixture so that bands of similarly sized polynucleotides are formed;

illuminating with an illumination beam the bands on the gel, the illumination beam being capable of causing the dyes to fluoresce; and identifying the class of the polynucleotides in the bands by the fluorescence or absorption spectrum of the dyes.

6. The method of claim 5 wherein each polynucleotide of said first class is labeled by attaching said first dye to said 3'-terminal dideoxyadenosine by way of a linking group, each polynucleotide of said second class is labeled by attaching said second dye to said 3'-terminal dideoxythymidine by way of a linking group, each polynucleotide of said third class is labeled by attaching said third dye to said 3'-terminal dideoxyguanosine by way of a linking group, and each polynucleotide of said fourth class is labeled by attaching said fourth dye to said 3'-terminal dideoxycytosine by way of a linking group.

7. The method of claim 6 wherein said dideoxyadenosine is 2',3'-dideoxy-7-deazaadenosine, said dideoxycytidine is 2',3'-dideoxycytidine, said dideoxyguanosine is 2',3'-dideoxy-7-deazaguanosine or 2',3'-dideoxy-7-deazainosine, and said dideoxythymidine is 2',3'-dideoxyuridine.

8. The method of claim 7 wherein said linking group links a 5 carbon of said 2',3'-dideoxycytidine or 2',3'-dideoxyuridine to a 5 or 6 carbon of said second dye or said fourth dye, respectively, and wherein said linking group links a 7 carbon of said 2',3'-dideoxy-7-deazaadenosine or 2',3'-dideoxy-7-guanosine or 2',3'-dideoxy-7-deazainosine to a 5 or 6 carbon of said first dye or said third dye, respectively.

9. The method of claim 8 wherein said linking group is carboxyaminoalkynyl.

10. The method of claim 9 wherein said carboxyaminoalkynyl is 3-carboxyamino-1-propynyl.

11. The method of claim 5 wherein said dideoxyadenosine is 2',3'-dideoxy-7-deazaadenosine, said dideoxycytidine is 2',3'-dideoxycytidine, said dideoxyguanosine is 2',3'-dideoxy-7-deazaguanosine or 2',3'-dideoxy-7-deazainosine, and said dideoxythymidine is 2',3'-dideoxyuridine.

12. The method of claim 11 wherein said first dye is 2',7'-dimethoxy-5-carboxy-4,7-dichlorofluorescein, said fourth dye is 5-carboxy-4,7-dichlorofluorescein, said third dye is 2',7'-dimethoxy-4',5'-dichloro-6-carboxy-4,7-dichlorofluorescein or 1',2',7',8'-dibenzo-4',5'-dichloro-5-carboxy-4,7-dichlorofluorescein, and said second dye is 1',2',7',8'-dibenzo-5-carboxy-4,7-dichlorofluorescein.

13. In a chain termination method of DNA sequencing, the method of the type wherein four classes of DNA fragments are formed such that DNA fragments of the same class have the same terminating base and are labelled with the same fluorescent dye, an improvement comprising:

labelling DNA fragments of at least one class with a 4,7-dichlorofluorescein dye selected from the group defined by the formula:

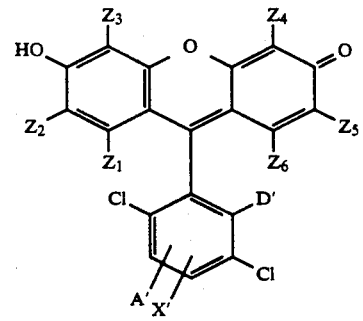

wherein:
A' is hydrogen, fluoro, chloro, or a group that may be converted to a linking functionality;
D' is fluoro, chloro, or an acidic anionic group;
X' is hydrogen, fluoro, or chloro;
Z' is hydrogen or, when taken with $Z_2$, benzo;
$Z_2$, when taken along, is hydrogen, halo, lower alkyl, lower alkyloxy, or a group that may be converted to a linking functionality, or when taken with $Z_1$, $Z_2$ is benzo;
$Z_3$ and $Z_4$ are separately hydrogen, halo, lower alkyl, lower alkyloxy, or a group that may be converted to a linking functionality;
$Z_6$ is hydrogen or, when taken with $Z_5$, benzo;
$Z_5$, when taken alone, is hydrogen, halo, lower alkyl, lower alkyloxy, or a group that may be converted to a linking functionality, or when taken with $Z_6$, benzo; and wherein only one of A', $A_2$, $Z_3$, $Z_4$, and $Z_5$ is a group that may be converted to a linking functionality.

14. The method of claim 13 wherein A' and D' are carboxyl; X' is hydrogen; $Z_2$, when taken alone, is hydrogen, chloro, methyl, ethyl, ethoxy, or methoxy; $Z_3$ and $Z_4$ are separately hydrogen, chloro, methoyl, ethyl, methoxy, or ethyoxy; and $Z_5$, when taken alone, is hydrogen, chloro, methyl, ethyl, ethoxy, or methoxy.

15. The method of claim 14 wherein $Z_1$, $Z_3$, $Z_4$, and $Z_6$ are hydrogen, and $Z_2$ and $Z_5$ are methoxy.

16. The method of claim 14 wherein $Z_1$ and $Z_6$ are hydrogen, $Z_3$ and $Z_4$ are chloro, and $Z_2$ and $Z_5$ are methoxy, or wherein $Z_1$ and $Z_2$ are benzo, $Z_5$ and $Z_6$ are benzo, and $Z_3$ and $Z_4$ are chloro.

17. The method of claim 14 wherein $Z_1$ and $Z_2$ taken together are benzo, $Z_5$ and $Z_6$ taken together are benzo, and $Z_3$ and $Z_4$ are hydrogen.

18. The method of claim 14 wherein $R_1$, $R_2$, $R_3$, $R_4$, $R_5$, and $R_6$ are hydrogen.

* * * * *

UNITED STATES PATENT AND TRADEMARK OFFICE
CERTIFICATE OF CORRECTION

PATENT NO. : 5,188,934
DATED : Feb. 23, 1993
INVENTOR(S) : Menchen et al.

It is certified that error appears in the above-indentified patent and that said Letters Patent is hereby corrected as shown below:

Claim 2, line 2, "B' is carboxyl . . ." should be "D' is carboxyl . . ."

Claim 13, line 29, "Z' is" should be "$Z_1$ is".

Claim 13, line 30, "when taken along" should read "when taken alone".

Claim 13, line 41, "only one of A', $A_2$, $Z_3$, $Z_4$. . ." should read "only one of A', $Z_2$, $Z_3$, $Z_4$. . .".

Signed and Sealed this

Twenty-sixth Day of October, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,188,934
DATED : February 23, 1993
INVENTOR(S) : Menchen et al.

Page 1 of 2

It is certified that error appears in the above-identified patent and that said Letters Patent is hereby corrected as shown below:

Title page,
Under "Other Publications", first reference, insert -- , pp. -- after "7(3) [vol.(issue)]";

Column 3,
Line 18, delete "A" and insert therefor -- $A'$ --;
Line 34, delete "group;";
Lines 36 and 37, delete "$B'$" and insert therefor -- $D'$ --;
Line 48, delete "4,7-chloro-5-" and insert therefor -- 4,7-dichloro-5- --;

Column 4,
Line 25, delete "4,7-chloro-5-" and insert therefor -- 4,7-dichloro-5- --;
Line 59, delete "$Z_5$ is hydrogen or, when taken with $Z_6$" and insert therefor -- $Z_6$ is hydrogen or, when taken with $Z_5$ --;
Line 60, delete "$Z_6$, when taken alone" and insert therefor -- $Z_5$, when taken alone --;
Line 64, delete "or when taken with $Z_5$," and insert therefor -- or when taken with $Z_6$ --;
Line 65, delete "$Z_6$ is benzo; preferably, when taken alone, $Z_6$" and insert therefor -- $Z_5$ is benzo; preferably, when taken alone, $Z_5$ --;

Column 5,
Line 10, delete "A=B-" and insert therefor -- $A=D'$ --;
Line 15, delete "A or B" and insert therefor -- A or $D'$ --;
Line 18, delete "or or" and insert therefor -- or --;

Column 9,
Line 4, delete "3,3" and insert therefor -- 3.3 --;
Line 5, delete "6,4" and insert therefor -- 6.4 --;
Lines 15, 16, and 18, delete every occurrence of "ul" and insert therefore -- µl --;
Line 35, delete "1,47" and insert therefor -- 1.47 --;

UNITED STATES PATENT AND TRADEMARK OFFICE
CERTIFICATE OF CORRECTION

PATENT NO.    : 5,188,934
DATED         : February 23, 1993
INVENTOR(S)   : Menchen et al.

It is certified that error appears in the above-identified patent and that said Letters Patent is hereby corrected as shown below:

Column 10,
Lines 35 and 36, delete every occurrence of "ul" and insert therefore -- $\mu l$ --;

Column 14, claim 14,
Line 47, delete "methoyl" and insert therefor -- methyl --;

Column 14, claim 18,
Lines 59 and 60, delete "$R_1$, $R_2$, $R_3$, $R_4$, $R_5$, and $R_6$" and insert therefor
-- $Z_1$, $Z_2$, $Z_3$, $Z_4$, $Z_5$, and $Z_6$ --.

Signed and Sealed this

Twenty-seventh Day of November, 2001

*Attest:*

*Attesting Officer*

NICHOLAS P. GODICI
*Acting Director of the United States Patent and Trademark Office*